United States Patent
Ito et al.

(10) Patent No.: US 10,715,021 B2
(45) Date of Patent: Jul. 14, 2020

(54) MOBILE CAPSULE DEVICE AND CONTROL METHOD THEREOF

(71) Applicant: KYUSHU INSTITUTE OF TECHNOLOGY, Kitakyushu-shi, Fukuoka (JP)

(72) Inventors: Takahiro Ito, Iizuka (JP); Sunao Murakami, Iizuka (JP)

(73) Assignee: KYUSHU INSTITUTE OF TECHNOLOGY, Kitakyushu-shi (JP)

( * ) Notice: Subject to any disclaimer, the term of this patent is extended or adjusted under 35 U.S.C. 154(b) by 947 days.

(21) Appl. No.: 14/371,493

(22) PCT Filed: Jul. 18, 2013

(86) PCT No.: PCT/JP2013/069536
§ 371 (c)(1),
(2) Date: Jul. 10, 2014

(87) PCT Pub. No.: WO2014/014062
PCT Pub. Date: Jan. 23, 2014

(65) Prior Publication Data
US 2014/0378760 A1   Dec. 25, 2014

(30) Foreign Application Priority Data
Jul. 20, 2012   (JP) .................................. 2012-161209

(51) Int. Cl.
*H02K 33/14*      (2006.01)
*A61B 5/06*       (2006.01)
(Continued)

(52) U.S. Cl.
CPC ......... *H02K 33/14* (2013.01); *A61B 1/00156* (2013.01); *A61B 1/00158* (2013.01);
(Continued)

(58) Field of Classification Search
CPC .... H02K 33/14; H02K 33/16; A61B 1/00158; A61B 1/041; A61B 1/00156
See application file for complete search history.

(56) References Cited

U.S. PATENT DOCUMENTS 5,510,660 A * 4/1996 Flatau ..................... H01L 41/12
                                                          310/26
6,639,496 B1 * 10/2003 van Namen ............ E05B 47/00
                                                          335/229
(Continued)

FOREIGN PATENT DOCUMENTS

CN        1968648 A      5/2007
CN      101282677 A     10/2008
(Continued)

OTHER PUBLICATIONS

Office Action dated Nov. 28, 2017, issued in counterpart Japanese Application No. 2014-525867, with English translation (11 pages).
(Continued)

*Primary Examiner* — Timothy J Neal
*Assistant Examiner* — Jae Woo
(74) *Attorney, Agent, or Firm* — Westerman, Hattori, Daniels & Adrian, LLP

(57) ABSTRACT

A mobile capsule device 10 comprises a long capsule body 11 having a permanent magnet 13 movable in the lengthwise direction with respect to the long capsule body and a coil for driving the permanent magnet 13, while a propulsion force is generated entirely by applying an alternate current to the coil and performing back and forth movements of the permanent magnet 13. The coil has first and second coil parts 15 and 16 arranged circumferentially in front and back of the permanent magnet 13, and a frequency of an alternate current applied to the first and second coil parts 15 and 16 is made to accord with a resonance frequency of the capsule device 10 generated by a back and forth vibration of the
(Continued)

permanent magnet 13. Thereby, a self-propelled, mobile capsule device 10 which is downsized, compact and efficient and a control method thereof can be provided.

6 Claims, 9 Drawing Sheets

(51) Int. Cl.
    *A61B 1/00*         (2006.01)
    *A61B 1/04*         (2006.01)
    *H02K 33/16*       (2006.01)
    *A61B 10/02*       (2006.01)
    *A61M 31/00*       (2006.01)
    *A61B 5/07*         (2006.01)

(52) U.S. Cl.
    CPC .............. *A61B 1/041* (2013.01); *A61B 5/065* (2013.01); *A61B 10/0266* (2013.01); *A61M 31/002* (2013.01); *H02K 33/16* (2013.01); *A61B 5/06* (2013.01); *A61B 5/061* (2013.01); *A61B 5/073* (2013.01); *A61B 2562/162* (2013.01)

(56) References Cited

U.S. PATENT DOCUMENTS

| | | | | |
|---|---|---|---|---|
| 6,975,055 | B2* | 12/2005 | Joong | B61C 9/48 310/114 |
| 9,375,202 | B2* | 6/2016 | Swain | A61B 10/02 |
| 9,509,202 | B2* | 11/2016 | Kawarai | H02K 35/02 |
| 2005/0200207 | A1* | 9/2005 | Hasegawa | H02K 33/16 310/10 |
| 2005/0216231 | A1 | 9/2005 | Aoki et al. | |
| 2008/0177178 | A1 | 7/2008 | Aoki et al. | |
| 2008/0227394 | A1* | 9/2008 | Homan | A61B 1/00016 455/41.3 |
| 2009/0093678 | A1 | 4/2009 | Kimura et al. | |
| 2009/0281387 | A1* | 11/2009 | Takizawa | A61B 1/00082 600/117 |
| 2010/0001592 | A1* | 1/2010 | Kawano | H02K 49/10 310/12.14 |
| 2010/0306934 | A1* | 12/2010 | Headstrom | A61C 17/221 15/22.2 |
| 2012/0061893 | A1* | 3/2012 | Hochberg | F03G 7/08 267/195 |
| 2012/0194008 | A1* | 8/2012 | Iijima | H02K 35/02 310/30 |
| 2013/0137921 | A1* | 5/2013 | Angot | A61B 1/00156 600/109 |
| 2017/0117771 | A1* | 4/2017 | Orand | H02K 5/08 |
| 2017/0360283 | A1* | 12/2017 | Kimura | A61B 1/00 |

FOREIGN PATENT DOCUMENTS

| | | |
|---|---|---|
| EP | 2 429 385 B1 | 7/2013 |
| JP | 4-176443 A | 6/1992 |
| JP | 5-212093 A | 8/1993 |
| JP | 6-133925 A | 5/1994 |
| JP | 2003-265403 A | 9/2003 |
| JP | 2003-265404 A | 9/2003 |
| JP | 2004-050154 A | 2/2004 |
| JP | 2006-280638 A | 10/2006 |
| JP | 2006-305695 A | 11/2006 |
| JP | 2007-151729 A | 6/2007 |
| JP | 2011-183374 A | 9/2011 |
| JP | 4847520 B2 | 12/2011 |
| JP | 2012-034561 A | 2/2012 |
| JP | 2013-111255 A | 6/2013 |
| WO | 2005/120345 A2 | 12/2005 |

OTHER PUBLICATIONS

International Search Report dated Aug. 20, 2013, issued in corresponding application No. PCT/JP2013/069536.
Mizuno et al., "Development of Capsule Endoscope Self-propelled by Linear Motor Mechanism", The Japanese Journal of Medical Instrumentation, 2011, pp. 181-187, vol. 81, No. 3, cited in the ISR.
Partial Supplementary European Search Report dated May 29, 2015, issued in counterpart European Patent Application No. 13820643.8 (6 pages).
Office Action dated Jun. 10, 2015, issued in counterpart Chinese Patent Application No. 201380004596.6, with English translation (10 pages).

* cited by examiner

MOBILE CAPSULE DEVICE AND CONTROL METHOD THEREOF

TECHNICAL FIELD

The present invention is used, for example, when examinations of gastrointestinal system are performed, and relates to a capsule device which incorporates a built-in camera or the like and moves independently, and a control method thereof.

BACKGROUND ART

Currently, microcapsules for interior observations and microscopic operations in narrow spaces performed in the examinations of gastrointestinal tracts or the like in the medical field are proposed, for example, in Patent Documents 1 to 3.

As to a medical capsule in Patent Document 1, an inertial body is vibrated by using piezoelectric elements. A capsule body receives a frictional force between the capsule and a biological body, and the medical capsule is moved forward. Additionally, as to an automatic traveling capsule device in Patent Document 2, it is disclosed that a capsule is moved forward by repeated energization and de-energization of a shape-memory alloy (SMA) wire, and also that a capsule is moved forward by the generation of a vibrating source for the forward and backward movements by using a coil and a permanent magnet.

Moreover, as to a traveling capsule in Patent Document 3, Patent Document 3 discloses that a permanent magnet and a coil are inserted in the capsule, and an alternating current is applied to the coil for a piston movement.

CITATION LIST

Prior Art Documents

Patent Literature

[Patent Document 1]
Japanese Unexamined Patent Application Publication No. 4-176443
[Patent Document 2]
Japanese Unexamined Patent Application Publication No. 5-212093
[Patent Document 3]
Japanese Unexamined Patent Application Publication No. 2006-280638

SUMMARY OF INVENTION

Technical Problem

Problems to be Resolved by the Invention

However, as to a technique described in Patent Document 1, though an inertial body is vibrated with the use of piezoelectric element, the vibration frequency thereof is relatively large and the force is weak, which leads to a weak advancing force, and there is a limit in making the speed at which the capsule self-propels faster. Enlarging a device, of course, empowers a self-propulsion force, however, an enlarged device does not fit into a small capsule.

As to a technique described in Patent Document 2, there is a problem that a drive force thereof becomes relatively weak and the efficiency is lowered when a shape-memory alloy (SMA) is used. Additionally, as to Patent Document 2, vibration using suction and repulsion of a coil and permanent magnet gives out relatively large amplitude, however, it is inefficient since there is only one coil.

Moreover, similarly, as to a technique described in Patent Document 3, a permanent magnet and a coil arranged opposite from each other are used, however, there is a problem that an attraction force and repulsion force between the permanent magnet and the coil become weak and the efficiency thereof is lowered when the permanent magnet is arranged far from the coil.

Furthermore, in vibration mechanisms using a coil and a permanent magnet in Patent Documents 2 and 3, there is no description regarding resonance phenomenon.

Inventors of the present invention arranged a coil on a cylindrical shell region, and made a permanent magnet, that is, a needle, perform a reciprocating movement by applying an alternating current, and by using an inertia force from the move of the needle and impact force generated from the needle's crashing into external walls, aggressively conducted a research on a capsule device that travels unidirectionally and achieved the present invention.

The inventors of the present invention also confirmed that arranging a permanent magnet inside a cylindrical coil, fixing the permanent magnet on the capsule body and applying an alternate current to the coil made the coil vibrate, and also made the capsule body vibrate in response.

The present invention has been made in view of the above circumstances, and the purpose of the present invention is to provide a downsized, compact and efficient capsule device that self-propels, and a control method thereof.

Solution to Problem

Means of Solving the Problems

In order to accomplish the above mentioned purpose, a first aspect of the present invention provides a mobile capsule device comprising a long capsule body provided with a permanent magnet and a coil, the permanent magnet being movable in the lengthwise direction with respect to the capsule body, the coil driving the permanent magnet, the coil being applied an alternate current through an alternate current generating means to perform a back and forth vibration of the permanent magnet and generate a propulsion force entirely, wherein the coil possesses first and second coil parts arranged circumferentially in front and back of the permanent magnet, and a frequency of an alternate current applied to the first and second coil parts are made to accord with a resonance frequency of the capsule device generated by the back and forth vibration of the permanent magnet.

Here, the present invention is applicable even when a frequency of an alternate current is in the range of ±10% of a resonance frequency of the entire capsule (or permanent magnet) (the same applies to the following invention).

In the mobile capsule device according to the first aspect of the present invention, it is preferred that the first and second coil parts be wound around a cylinder-shaped body (usually referred to as a bobbin) having a slight interspace to enable the inside move of the permanent magnet, stoppers be mounted on both sides of the cylinder-shaped body, and the permanent magnet vibrate while crashing into the stoppers. Moreover, the preferable constituent of the cylinder-shaped body is non-magnetic substance, however, it can also consist of either a conductor (e.g., aluminum) or an insulator (the same applies to the inventions below).

In the capsule device according to the first aspect of the present invention, it is preferred that an alternate current generated by an alternate current generating means be composed of a positive/negative symmetric alternating current that is added by a direct current, an excitation force generated by the first and second coil parts and the permanent magnet be intensified in one direction, and the moving direction of the capsule device be determined based on a polar character of the direct current.

In the mobile capsule device according to the first aspect of the present invention, it is preferred that an alternate current applied to the first and second coil parts be determined by actually applying an alternate current to the first and second coil parts, and based on the value at which an electric current value thereof becomes minimum. It is technically easy to calculate a resonance frequency with this.

A mobile capsule device according to a second aspect of the present invention comprises a long capsule body having permanent magnets and a coil, the permanent magnets of which a magnetic pole aligned in the lengthwise direction with respect to the long capsule body, the coil being wound around with an interspace between the permanent magnet and the coil and receiving an electricity supply of an alternate current through an alternate current generating means, wherein at least two bar-like magnets of the permanent magnets are arranged opposed to each other with the same polarity, and a frequency of the alternate current is made to accord with a resonance frequency of a back and forth vibration of the coil (or capsule body of the same frequency) arranged so as to be able to slide.

In the mobile capsule device according to the second aspect of the present invention, it is preferred that an alternate current applied to the coil be determined by actually applying an alternate current to the coil, and based on the value at which an electric current value thereof becomes minimum.

In the mobile capsule device according to the second aspect of the present invention, it is preferred that the coil be wound around a cylinder-shaped body capable of performing a slide movement with respect to the bar-like magnets.

In the mobile capsule device according to the second aspect of the present invention, the coil sometimes has first and second coil parts arranged apart from each other on the cylinder-shaped body.

In the mobile capsule device according to the second aspect of the present invention, it is preferred that an alternate current generated by the alternate current generating means be composed of a positive/negative symmetric alternate current added by a direct current, an excitation force generated by the coil and the permanent magnet be intensified in one direction, and the moving direction of the capsule device be determined based on a polar character of the direct current.

In the capsule device according to the first and second aspects of the present invention, it is preferred that the capsule body be provided with a radio liaised with an external control device. It is also preferred that the coil be used as an antenna for the radio.

In the mobile capsule device according to the first and second aspects of the present invention, it is preferred that the capsule body be provided with one or more of the following: an illuminated microcamera, instrument for procedures, dosing feature, and position sensor.

A control method for a mobile capsule device according to a third aspect of the present invention comprises a long capsule body provided with a permanent magnet and a coil, the permanent magnet movable in the lengthwise direction with respect to the capsule body, the coil driving the permanent magnet, the coil being applied an alternate current to the coil to perform a back and forth vibration of the permanent magnet and generate a propulsion force entirely, wherein the moving direction of the capsule body is determined by making a frequency of an alternate current applied to the coil accord with a resonance frequency of a back and forth vibration of the permanent magnet and superposing a direct current on the alternate current.

In the control method for a mobile capsule device according to the third aspect of the present invention, it is preferred that the coil be divided for first and second coil parts each arranged in front and back of the permanent magnet, the first and second coil parts be wound around a cylinder-shaped body with an interspace to enable the inside slide movement of the permanent magnet, and the permanent magnet be made to perform a back and forth vibration with respect to the cylinder-shaped body.

A control method for a mobile capsule device according to a fourth aspect of the present invention comprises a long capsule body having permanent magnets and a coil, the permanent magnets of which a magnetic pole aligned in the lengthwise direction with respect to the capsule body, the coil being wound around the permanent magnet with an interspace between the coil and the permanent magnet, the coil being applied an alternate current to perform a back and forth vibration of the coil and generate a propulsion force entirely, wherein at least two bar-like magnets of the permanent magnets are arranged opposed to each other with the same polarity, and the moving direction of the capsule body is determined by making a frequency of an alternate current applied to the coil accord with a resonance frequency of a back and forth vibration of the coil and superposing a direct current on the alternate current.

In the control method for a mobile capsule device according to the third and fourth aspects of the present invention, it is preferred that an interior portion of a capsule body be provided with one or more of the following: an illuminated microcamera, instrument for procedures, dosing feature and position sensor. It is also preferred that controls be performed by a radio that uses the coil as an antenna and a control part connected to the radio.

Advantageous Effects of Invention

Effect of the Invention

In the mobile capsule device according to the first and second aspects of the present invention and the control method for a mobile capsule device according to the third and fourth aspects of the present invention, since a frequency of an alternate current applied to a coil is made to accord with a resonance frequency generated by a back and forth vibration of a permanent magnet or the coil, as the flow of an electric current decreases, vibration with maximum amplitude (piston movement) can be obtained by using the reduced electric current. Therefore, the capsule device can move with less electric power.

Especially, by dividing the coil for driving the permanent magnet for the first and second coil parts arranged in front and back of the permanent magnet, the coil generates an attracting force and repulsive force, enabling the permanent magnet or coil to vibrate more efficiently with less electric power.

Moreover, by decreasing the number of coil turns as compared to the case where the coil is wound around continuously in the lengthwise direction of a capsule body, heat-induced temperature rise in a capsule device can be prevented.

Additionally, by superposing a direct current on an alternate current applied to a coil, an excitation force of one side can be more intensified than the other, enabling an acceleration of one-direction movement of a capsule device. In this case, a circuit can be composed of a combination of a circuit which generates an alternate current (including a square wave) and a circuit which generates a direct current, resulting in the simplification of the circuit as well.

DESCRIPTION OF EMBODIMENTS

Description of the Preferred Embodiments

Figure 1:
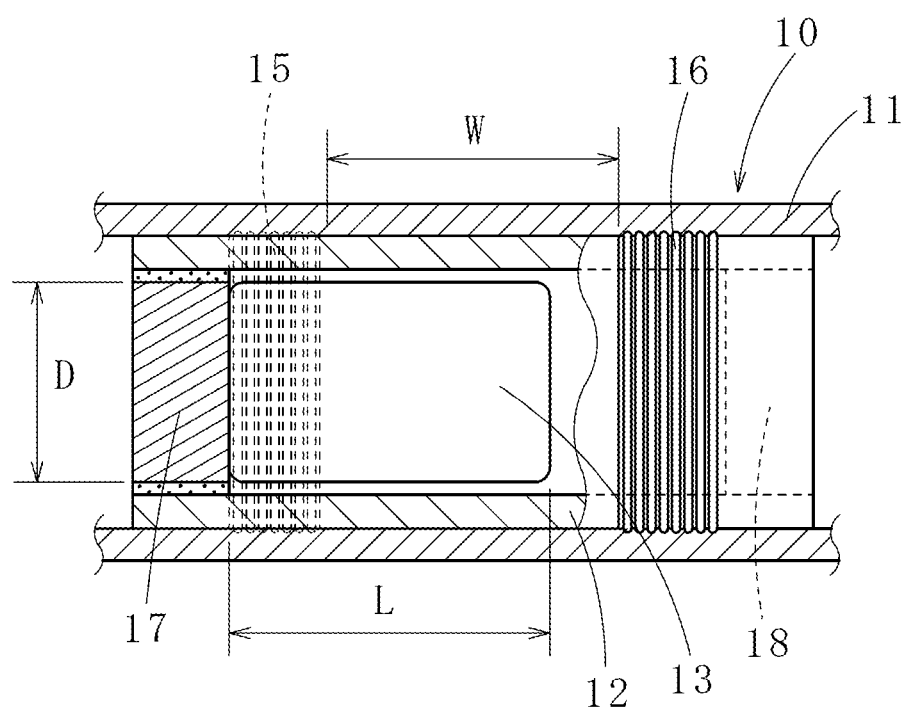
FIG. 1 is a cross-sectional view of a substantial part of a mobile capsule device related to a first embodiment of the present invention.

Next, with reference to attached drawings, embodiments concretizing the present invention will be described in detail. As illustrated in FIG. 1, a mobile capsule device (hereinafter referred to as a "capsule device") 10 according to a first embodiment of the present invention comprises a long capsule body 11, a bar-like permanent magnet 13, and first and second coil parts 15 and 16, the long capsule body 11 having a circular cross-section and of which a total length being longer than a radius of a cross-sectional surface thereof, the bar-like permanent magnet 13 arranged on the capsule body 11 through a cylinder-shaped body 12 and acting as a needle movable in the lengthwise direction with respect to the capsule body 11, and the first and second coil parts 15 and 16 (one example of a coil) being wound around both sides (front and back) of a bobbin consisting of the cylinder-shaped body 12 and arranged so as to surround the permanent magnet 13 and driving the permanent magnet 13. Explanations on above mentioned parts will be given hereinafter.

As a permanent magnet 13, for example, a neodymium magnet with the diameter D of approximately from 2.5 mm to 5 mm (3 mm in this embodiment) and the length L of from 7 mm to 15 mm (10 mm in this embodiment) is used, however, the neodymium magnet can be substituted by other materials as long as the materials are powerful permanent magnets. Moreover, the preferred interspace W between the first and second coil parts 15 and 16 is approximately from 10 mm to 20 mm.

The first and second coil parts 15 and 16, for example, are composed of cylinder-shaped bodies 12 with the inside diameter of D+0.1 mm (the outside diameter of, for example, D+1.1 mm) each wound 50 times by a conductor with the diameter of 0.05 mm, with a width of approximately from 2 mm to 4 mm between each wind. The interspace W between the first and second coil parts 15 and 16 is approximately 0.8 to 1.2 times the length L of the permanent magnet 13. Moreover, there is a total interspace of 0.1 mm in a radial direction between the inside diameter of the cylinder-shaped body 12 and the permanent magnet 13, so the permanent magnet 13 is able to move inside the cylinder-shaped body 12 without any resistance.

In this embodiment, the cylinder-shaped body 12 is composed of an aluminum pipe, and on both sides thereof, two stoppers 17 and 18 composed of either elastic member (e.g., gum, plastic) or metal are arranged (for example, with glue). There is a slight interspace formed inside to enable the permanent magnet 13 to move through a predetermined distance (in this embodiment, the predetermined distance is approximately 8 mm). Additionally, in an experiment explained below, a whole bobbin (the cylinder-shaped body 12) wound by the first and second coil parts 15 and 16 was put inside the capsule body 11 and the capsule device 10 (sometimes referred to as a "vibration motor") with the entire outside diameter of approximately 10 mm and the length of approximately 21 mm was used. As to the products that actually apply the present invention, measurements are not confined to the above measurements, and a diameter and a length are modifiable in accordance with each intended purpose. Moreover, it is possible to alter an end portion of the capsule body 11 to a hemispherical or lens-shaped member, in accordance with each intended purpose.

In the experiment, a low-frequency oscillator and an amplifier were used as an example of an alternate current generating means. As a low-frequency oscillator (multi-function generator), "WF19739" manufactured by NF Corporation was used, and as an amplifier to amplify waveforms, "BWA25-1" manufactured by Takasago Ltd. was used. These are for freely changing a frequency of an alternate current applied to first and second coil parts 15 and 16 and an output voltage in the experiment.

In order to make this vibration motor travel, an alternating current generated by the multifunctional generator and amplifier both explained above must be delivered to a coil composed of the first and second coil parts 15 and 16. By an electromagnetic force generated by the first and second coil parts 15 and 16, a needle inside (the permanent magnet 13) performs a back and forth vibration.

Figure 2:
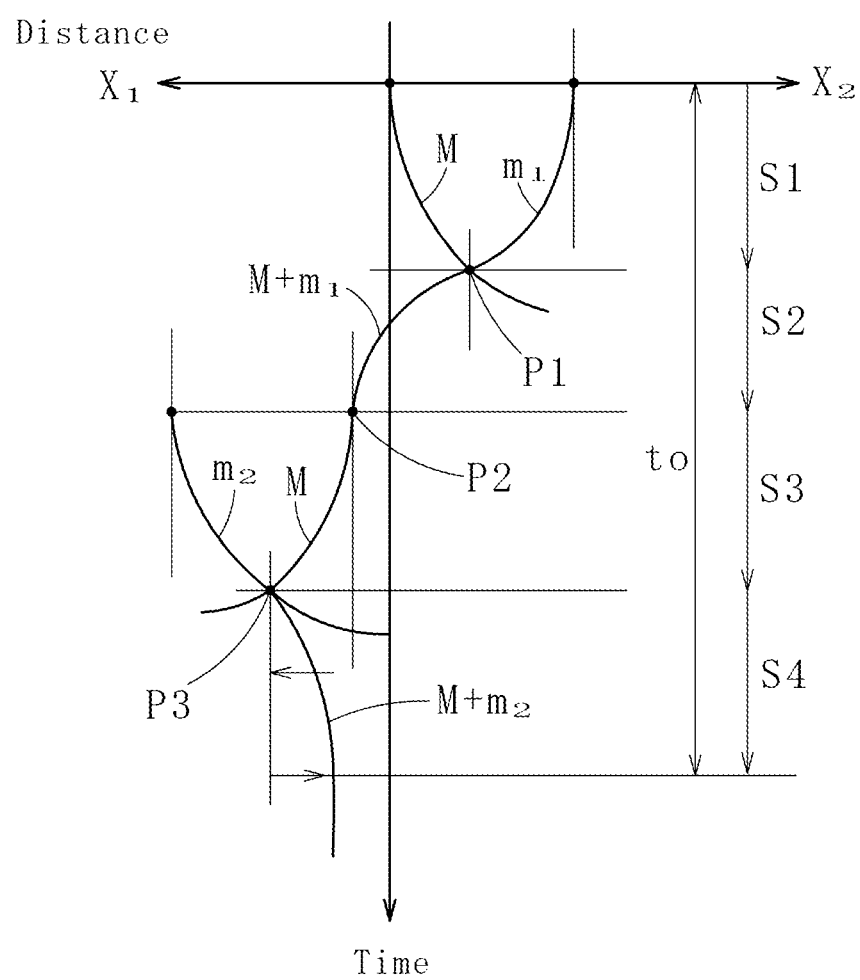
FIG. 2 is an explanatory drawing showing a movement of the mobile capsule device.

An explanation on this behavior will be given hereinafter by using FIG. 2. M indicates an outer shell (indicates a portion excluding the permanent magnet 13) in a resting state, m1 and m2 indicate the permanent magnet 13, and when a unidirectional electric current is applied to the first and second coil parts 15 and 16, the permanent magnet 13 indicated by m1 moves in the direction of X1, and the outer shell moves in the direction of X2 to attract one another (Step S1).

Then, at the point of P1, the permanent magnet 13 crashes into an outer bailey (stopper 17, in actuality), however, since the permanent magnet 13 possesses more energy than the outer bailey, the entirety is dragged even more and moved in the direction of X1 (Step S2).

Next, at the point of P2, the direction of an electric current applied to the first and second coil parts 15 and 16 is switched over. By this, the permanent magnet 13 moves to the direction of X2, and at the point of P3, crashes into the stopper 18 (the outer bailey) on the other side (Step S3). Moreover, the permanent magnet 13 in Steps S3 and S4 illustrated in FIG. 2 is placed away from m1 and indicated by m2.

After this, since the permanent magnet 13 possesses more energy, the permanent magnet 13 and outer shell are dragged back to or somewhere close to the initial position (Step S4). By repeating the above 4 processes, the outer shell including the stoppers 17 and 18, cylinder-shaped body 12 and capsule body 11 generates a force to move in the opposite direction of the needle's moving direction through a kinetic reaction of a needle (i.e., a force generated in a coil), and the needle crashes into the stoppers 17 and 18 to generate an intense impact force. With these forces applied, a vibration motor (i.e., a capsule device 10) performs movements. The code "to" indicates one period of vibration.

As to this capsule device 10, in relation to the movement of a needle, giving an AC (alternating-current) signal to a coil externally enables the needle and the capsule body 11 to repeatedly move back and forth, however, if the needle performs the repeated back and forth movements at equal speed, an equal amount of a kinetic reaction and impact force are applied in front and back, and this capsule device 10 vibrates only in one spot and cannot move back and forth. With that said, by changing a duty ratio (i.e., a ratio between positive and negative electric currents) of an AC signal input, a magnetic field produced by the coil can be shifted, and a mobile velocity of the needle inside a vibration motor can be varied in each direction. This makes the vibration motor, that is, this capsule device 10, generate a propulsion force in one direction, enabling the capsule device 10 to move back and forth.

Figure 3A:
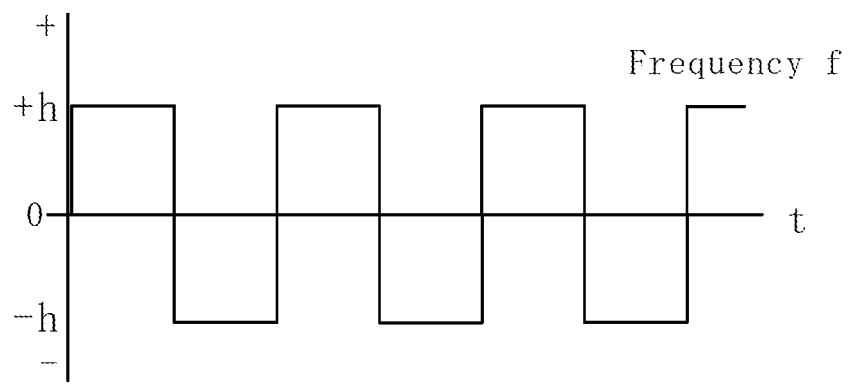
FIGS. 3(A), (B) and (C) are explanatory drawings showing a method of formation of a voltage added to a coil.
Figure 3B:
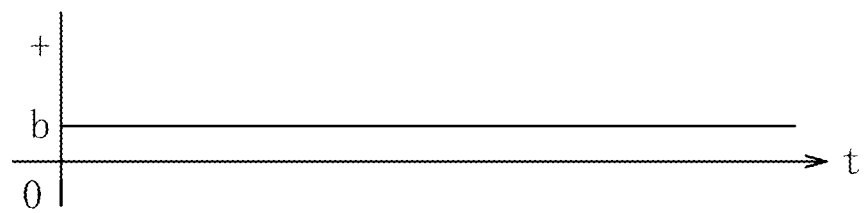
Figure 3C:
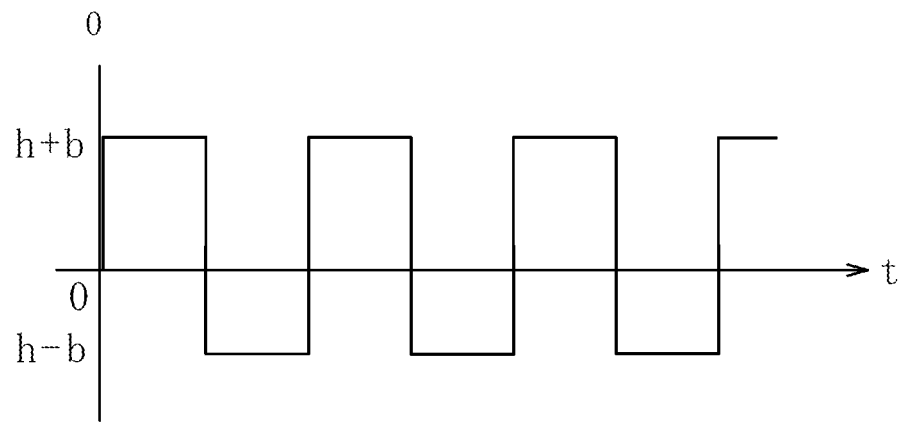

As a method for generating a foregoing AC signal, it is easily obtained by adding a direct current bias to an alternating current generated from the above-described low-frequency oscillator and amplifier. At the time of a vibration motor examination, a direct current frequency, output voltage and bias voltage were easily configured by using this method, however, it is not necessary to change the frequency and output voltage in an actual equipment. Therefore, as illustrated in FIG. 3(A), it is possible to generate a square-wave alternate current with positive/negative symmetrical predetermined frequency f and crest value h, and superpose a direct current (voltage b) on this as illustrated in FIG. 3(B), then form an alternate current of which the amount of electric current is larger in one direction (crest value h+b, h−b) as illustrated in FIG. 3(C). The alternate current generating means in this case is easily formed by using a digital signal. By changing a polar character (i.e., positive/negative direction) of the direct current at this point, the moving direction of this capsule device 10 is determined.

Moreover, since the first and second coil parts 15 and 16 are connected in series, force (an excitation force) acts on a permanent magnet 13 more intensely in one direction than the other, consequently enabling the capsule device 10 to move even faster. In this case, it is preferred that opposed inner end positions of the first and second coil parts 15 and 16 be arranged on each end of the permanent magnet 13 in the middle position.

Figure 4:
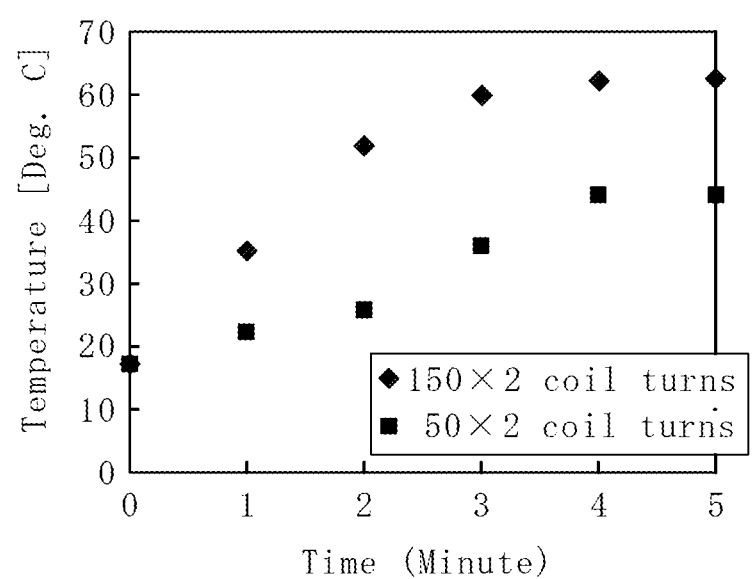
FIG. 4 is a graph showing a fluctuation in the surface temperature of an actuator (coil).

Next, FIG. 4 illustrates a result of a test on temperature rise in coils when the numbers of turns in first and second coil parts 15 and 16 were changed.

A non-contact thermometer was used for the temperature measurement, and a capsule device for the experiment of the first and second coil parts 15 and 16 with 150-turn×2 and 50-turn×2 was used. The measurement was conducted with the maximum power allowed to input to this capsule device: 0.5 amperes and 3.3 volts.

A voltage of +3.3 volts and a voltage of −3.3 volts were switched over to one another by 40 Hz and loaded on the first and second coil parts 15 and 16, and the temperature was kept measuring for 5 minutes until the surface temperature of an actuator (coil) became equalized.

The air temperature at the time of measurement was 18° C. As shown in FIG. 4, in the case of 150-turn×2 (300 turns), the temperature reached 63.3° C. after the five minutes of measuring, and in the case of 50-turn×2 (100 turns), the temperature reached 44.6° C. after the five minutes of measuring. Hence, in the present invention, considering the safety, the optimal number of coil turns was 50-turn×2 (100 turns) which had a smaller rise in temperature.

Next, a mobile velocity of this capsule device 10 was reviewed. The mobile velocity S of a vibration motor (capsule device 10) that vibrates by going through the process of Steps S1 to S4 can be calculated from the expression (1) below. Each code indicates the following:
a: Sum of displacement of vibration motor outer bailey and displacement of permanent magnet, $f_1$: Electromagnetic force in steps S1 and S2, $f_2$: Electromagnetic force in steps S3 and S4, T: Time of one cycle of pulse waveform which indicates the time taken for a needle to go through the behaviors of steps S1 to S4, n: Mo/m ("m"=mass of permanent magnet, and "Mo"=mass of entire capsule device−(subtracted by) m).

Example 1

[Mathematical 1]

$$S = \frac{2an(f_1 - f_2)}{\{(n+1)f_1 - 1\}\{(n+1)f_2 - 1\}T} \quad (1)$$

However, by using the above expression (1), a mobile velocity S is calculated based on the condition where a frequency of a direct current is constant, and any change in frequency results in a behavior change. In the experiment, by shifting a frequency from several Hz to approximately 100 Hz and observing a travel motion of the vibration motor, it was confirmed that there existed a frequency value that enabled the vibration motor to move the fastest. Machinery composed of springs and mass generally has a natural frequency thereof, and amplitude thereof becomes the largest when resonated.

Figure 5:
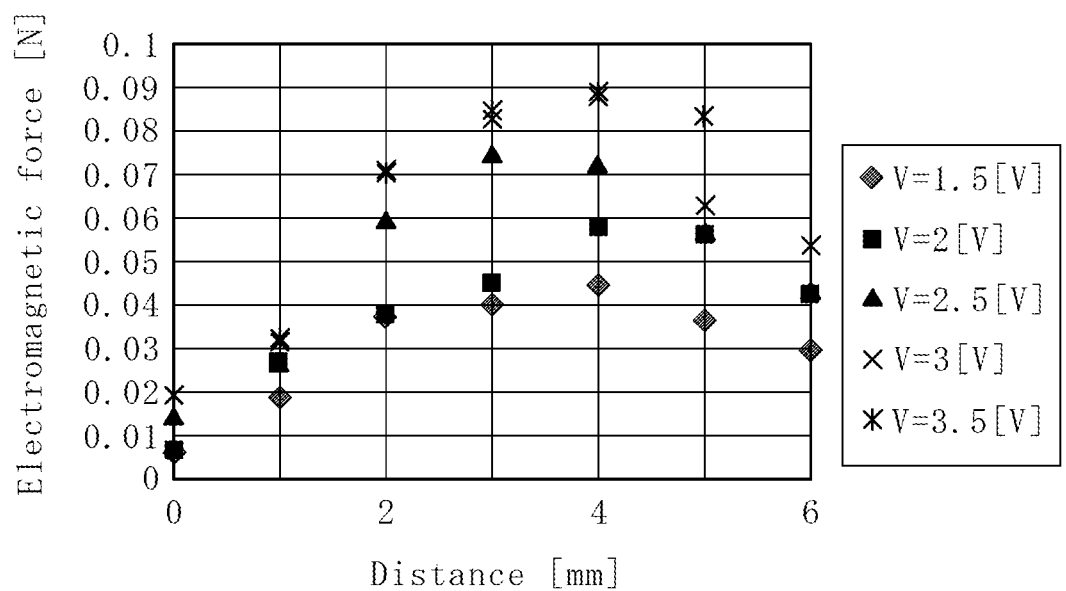
FIG. 5 is a graph showing a relationship between an electromagnetic force of the mobile capsule device and a distance.

FIG. 5 illustrates the characteristics of an electromagnetic force of a vibration motor, indicating a relationship between the distance (mm) from the center of first and second coil parts 15 and 16 to the center of a permanent magnet 13 and the electromagnetic force (N) while changing an electric current (direct current) applied to the first and second parts 15 and 16. Since the relationship between the distance and electromagnetic force is proportionate, consequently, the value calculated by dividing the electromagnetic force by the distance can be approximated to a spring constant K. With that, as a magnitude of the spring constant, according to a graph of 1.5 volts [V] in FIG. 5, let a rate of change be 0.04(N) with respect to the distance of 4 mm, and if the natural frequency f of simple harmonic motion is calculated from an expression (2) by using a needle mass of 20×0⁻⁴ (0.2 g), the answer is 35.6 Hz, which accords with the optimal frequency (i.e., resonance frequency) calculated in the experiment. Note: K=spring constant, m=mass of needle.

[Mathematical 2]

$$f = \frac{1}{2\pi}\sqrt{\frac{K}{m}} \qquad (2)$$

Moreover, as to this resonance frequency, when an alternate current is applied to first and second coil parts and a needle is made to vibrate, an electric current running through the first and second coil parts 15 and 16 becomes minimum. Therefore, it is easily detected.

Furthermore, when a reciprocation distance R (stroke) for a needle to move through by vibration is long, if a vibration frequency is high, increasing an amount of electric current applied to a coil does not help the needle reach stoppers 17 and 18 (i.e., the wall of outer shell) and the needle repeats a reciprocating movement without collision. In that case, the traveling speed is sometimes decreased. Thus, a limit of frequency until the needle reaches the stoppers 17 and 18 is calculated in order to prevent the needle from vibrating with a higher frequency. If R indicates stroke and f indicates frequency, a limiting frequency can be calculated by (f/2RM), and if the stroke R is substituted in an expression, the limiting frequency is 456 Hz. Therefore, the frequency value of 35.6 Hz enables the needle to reach the stoppers 17 and 18, and this was also confirmed in the experiment.

Figure 6:
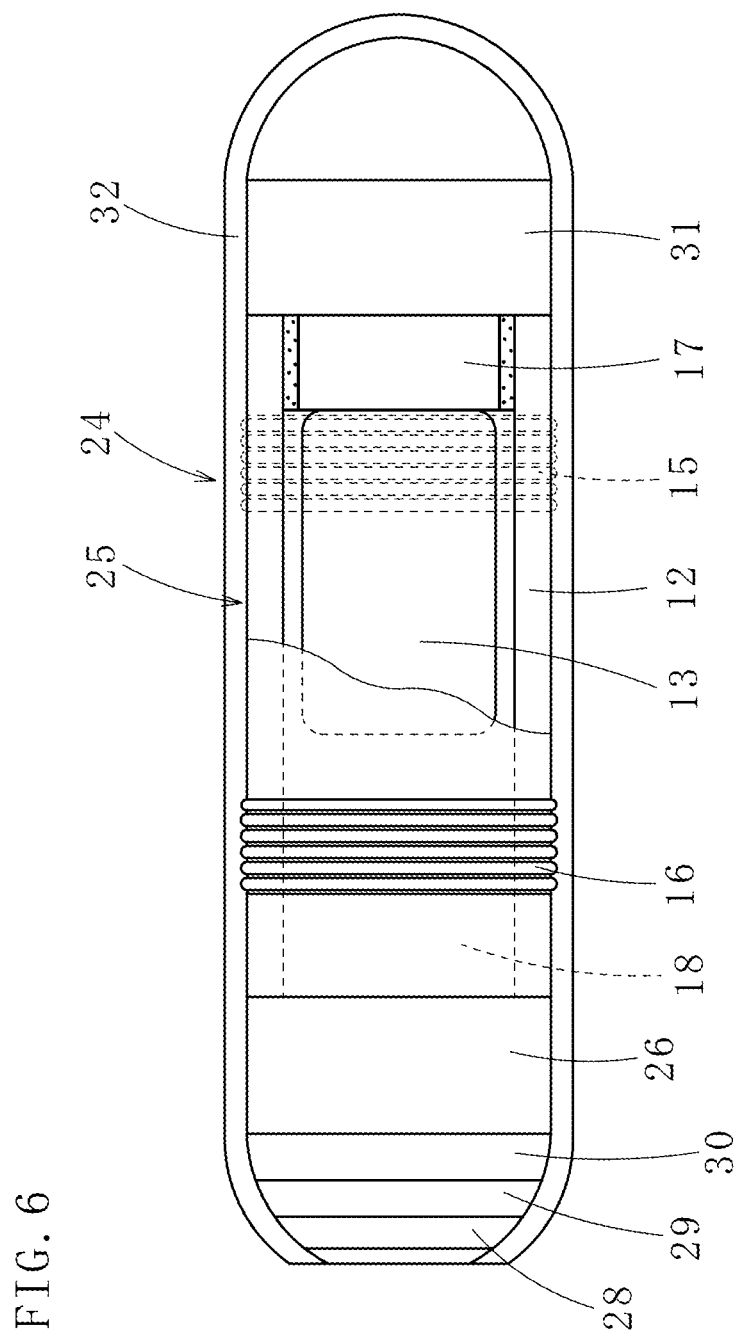
FIG. 6 is a cross-sectional view of a capsule device which was put into a practical use by an advancement of the mobile capsule device.

FIG. 6 illustrates a capsule device 24 that is a more embodied version of a whole apparatus, and inside a capsule body 32, there are an actuator 25 having a permanent magnet 13 and first and second coil parts 15 and 16, battery (electrical power supply) 26, illuminated microcamera 28, instrument for unillustrated procedures (e.g., collecting cells), dosing feature, position sensor 29, control system 30 for the previously mentioned members and radio 31 liased with external control systems. The detailed explanations on the illuminated microcamera 28, instrument for procedures, dosing feature and position sensor 29 are not given due to their well-recognized structure.

Next, with reference to FIGS. 7(A), 7(B), 7(C), FIG. 8 and FIG. 9, explanations on a mobile capsule device (hereinafter referred to as a "capsule device") 35 according to a second embodiment of the present invention will be given. As to the foregoing capsule device 10, a permanent magnet 13 vibrates and coils (first and second coil parts 15 and 16) are fixed, however, as to this capsule device 35, permanent magnets 39 and 40 are fixed and a circumferentially-placed coil 42 vibrates. There are common points in both capsule devices: the capsule body moves in one direction due to the reaction of a vibrating body arranged therein; and a resonance phenomenon is used for the vibration.

Figure 7A:
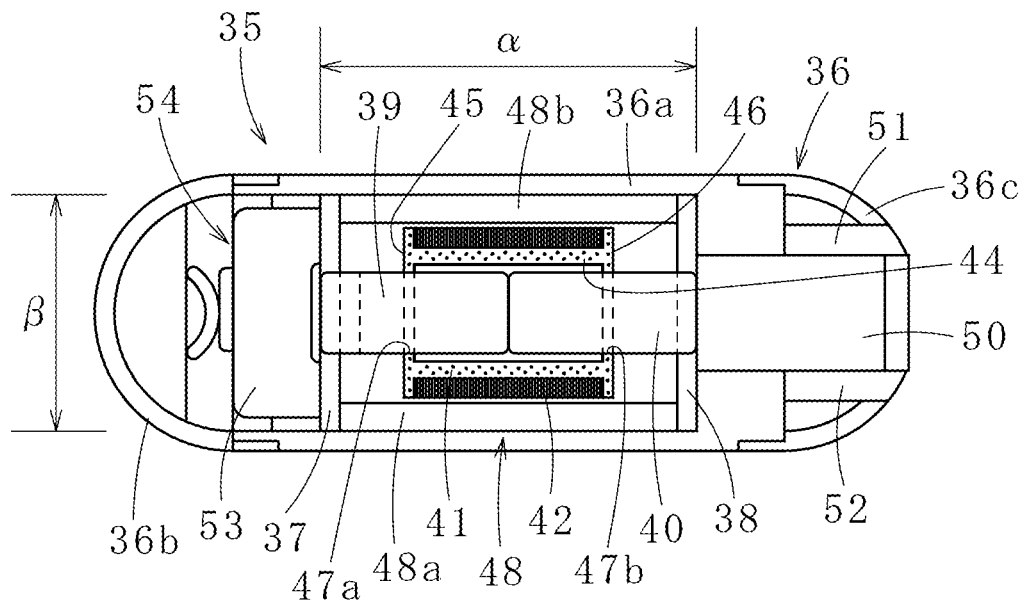
FIGS. 7(A) and (B) are cross-sectional views of substantial parts of the mobile capsule device related to a second embodiment of the present invention.
Figure 7B:
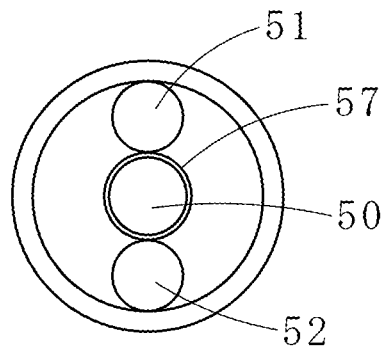
FIG. 7(C) is a perspective view.
Figure 7C:
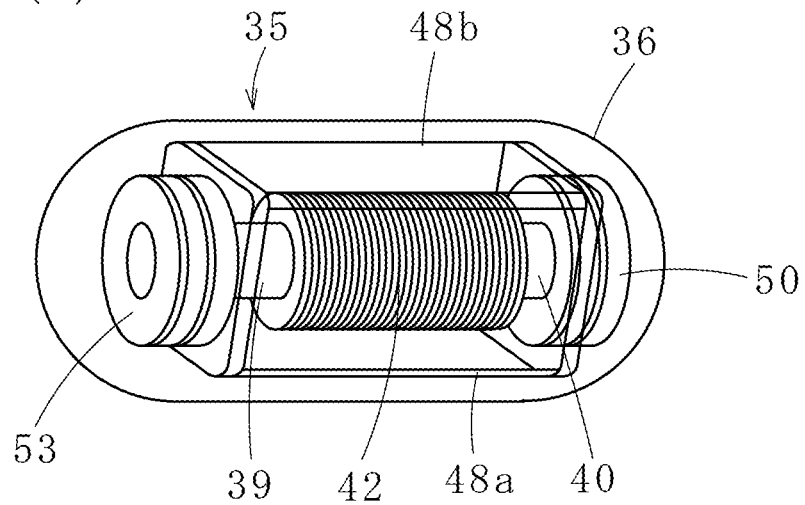
Figure 8:
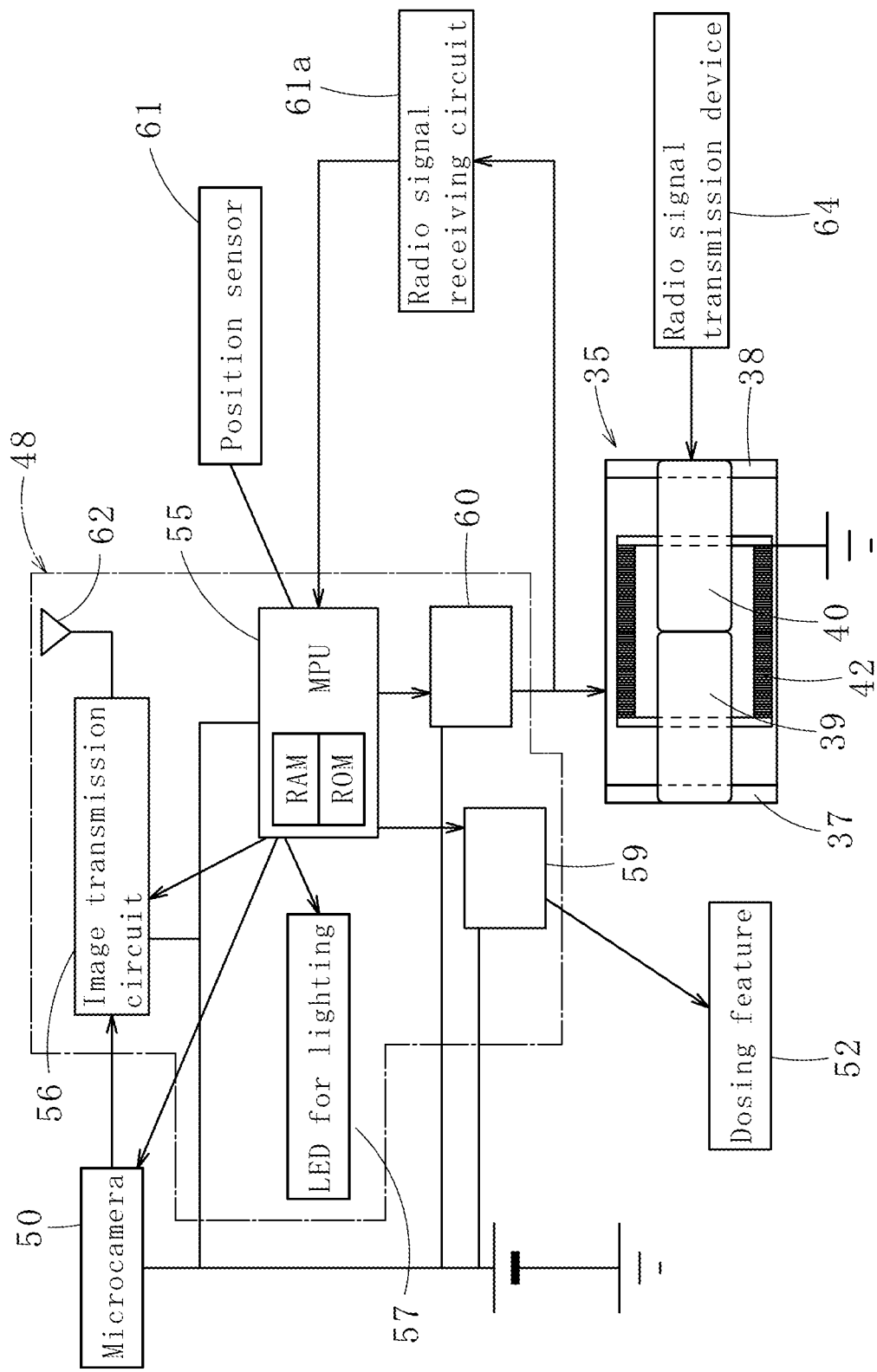
FIG. 8 is a block diagram of an electrical circuit of the mobile capsule device.

As illustrated in FIGS. 7(A) and 7(B), a capsule device 35 has a long capsule body 36, cylindrical permanent magnets 39 and 40 arranged inside the capsule body 36 through supporting members 37 and 38, a bobbin 41 which is an example of a cylinder-shaped body arranged on the outer side centering around the permanent magnets 39 and 40 so as to be able to perform slide movements, and a coil 42 which level-winds the bobbin 41. Here, the permanent magnets 39 and 40 are in the center of axis of the capsule body 36, with the magnetic poles aligned in the lengthwise direction of the capsule body 36.

The preferred diameter of the capsule body 36 is from 4 mm to 10 mm, and the preferred length thereof is approximately from 12 mm to 20 mm (end-to-end). The capsule body 36 should be made from materials that are harmless to human bodies, especially to the internal organs, such as plastic (e.g., acrylic, polycarbonate and polypropylene) and metal (e.g., aluminum and titanium). The capsule body 36 has a cylindrical portion 36a, and hemispherical lid portions 36b and 36c screwed on both sides of 36a.

Supporting members 37 and 38 are composed of disk-shaped plastic with the diameter 13 of, for example, approximately from 4 mm to 8 mm, and fixed inside of a cylindrical portion 36a of the capsule body 36. A total length α of the permanent magnets 39 and 40 is, for example, approximately from 10 mm to 15 mm.

The permanent magnets 39 and 40 arranged in the center of the axis of the capsule body 36 and in the middle portion of the longitudinal direction are composed of two same-size bar-like magnets made of neodymium magnets arranged opposed to each other with the same polarity (north pole or south pole). In this embodiment, the ends of the permanent magnets 39 and 40 of the same polarity are joined opposed to each other with glue to be integrated.

The bobbin 41 is composed of non-magnetic materials (e.g., plastic and aluminum), and has a cylindrical portion 44 and flanges 45 and 46 arranged on both sides of the cylindrical portion 44, and an inside diameter of the cylindrical portion 44 is longer than the diameter of the permanent magnets 39 and 40, however, the size of middle holes 47a and 47b of the flanges 45 and 46 is slightly (e.g., from 0.05 mm to 0.2 mm) larger than the outside diameter of the permanent magnets 39 and 40. Both sides of the bobbin 41 are temporarily supported by the permanent magnets 39 and 40 and the bobbin 41 is able to perform back and forth slide movements with respect to the permanent magnets 39 and 40.

A coil 42 winds a bobbin 41 symmetrically in the longitudinal direction, with both ends of the coil 42 fixed on the ends of the bobbin 41, and a copper wire on both ends is connected to a control part 48 fixed inside the capsule body 36 with some extra lengths (e.g., with some curled parts). Also, a thin enameled wire is used for the coil 42, with approximately from 50 to 100 coil turns, and both single-layer winding and multiple-layer winding are applicable. The coil 42 has curled parts which are the ends of a winding wire on both sides thereof, and is arranged in the intermediate portion of the capsule body 36, however, the position of the coil 42 can be determined by either arranging an elastic member on both sides or a magnetic absorbent material in the center of the bobbin.

An illuminated microcamera 50 is arranged on one side of a capsule body 36, an instrument for procedures (e.g., cutter and cell sampler) 51 and a dosing feature 52 on both sides of the illuminated camera, and a storage portion 54 for a battery 53 is arranged on the other side of the capsule body 36.

As illustrated in FIG. 7(A) to 7(C) and FIG. 8, a control part 48 is arranged on plate-like platforms 48a and 48b, and provided with MPU55 equipped with RAM and ROM, image transmission circuit 56 connected to the microcamera 50, LED for lighting 57 for the microcamera 50, and the first and second output parts 59 and 60.

Moreover, a capsule body 36 is also provided with a position sensor 61. The position sensor 61 detects the direction of the capsule body 36 and the rotation angle against shaft center, and the detected signals are transmitted to an image transmission circuit 56 and to the exterior with image signals. The angles of the photographing direction and circumferential direction of the microcamera 50 can accordingly be detected externally.

Furthermore, this position sensor 61 is not an essential factor in the present invention, and the direction of a capsule device 35 (same with 10) inside a human body can be detected by exteriorly arranged sensors such as an ultrasonic sensor, radio-frequency sensor and X-ray imaging device.

Moreover, platforms 48a and 48b are provided with a radio signal receiving circuit (an example of radios) 61a aside from (can be the same as) a control part 48, the radio signal receiving circuit receives radio signals from a radio signal transmission device 64 which is on the outside (i.e., external control device or controller), and is able to actuate the control part 48. Additionally, a coil 42 is used as an antenna for the radio signal receiving circuit 61a. Here, an image transmission circuit 56 is provided with an independent antenna 62, however, this can be substituted by the coil 42. Also, the radio signal receiving circuit 61a is interlinked with the control part 48 by the radio signals.

A first output part 59 is an amplifier for the actuation of a dosing feature 52, and the dosing feature 52 is turned on (opened) and off (closed) by amplifying signals from MPU 55.

A second output part 60 gains an output of a different duty ratio (a ratio between a positive-side signal and negative-side signal) as shown in FIG. 3(C) by superposing the direct current bias as shown in FIG. 3(B) on an AC signal received from MPU 55 as shown in FIG. 3(A). By this means, a signal from the coil 42 is biased in one direction, and the moving direction of the capsule device 35 is determined. It is preferred that the duty ratio be, for example, approximately from 1.1 to 1.4. The switchover between a forward movement and backward movement of the capsule device 35 is conducted by changing the direction of a direct current bias to be superposed. Additionally, MPU 55 and the second output part 60 operate as alternate current generating means.

If an alternate current is applied to the coil 42, since permanent magnets 39 and 40 are fixed, the coil 42 vibrates back and forth along the permanent magnets 39 and 40 just like a regular speaker. A resonance frequency is determined based on the minimum value of an electric current when an alternate current with a changed frequency is applied to the coil 42. An oscillation frequency can be changed by the operation of MPU 55, however, it is preferable to preliminary conduct an experiment, measure a resonance frequency of a back and forth vibration of the coil 42, and send a signal from MPU 55 to a second output part 60 according to the measured resonance frequency. The second output part 60 has an amplifier inside, and amplifies a faint signal from MPU 55 to a predetermined magnitude.

In this embodiment, the duty ratio is modulated by controlling an electric current (or voltage) of a direct current to be superposed, however, changing a temporal difference between on and off of a waveform can also modulate a duty ratio.

Figure 9:
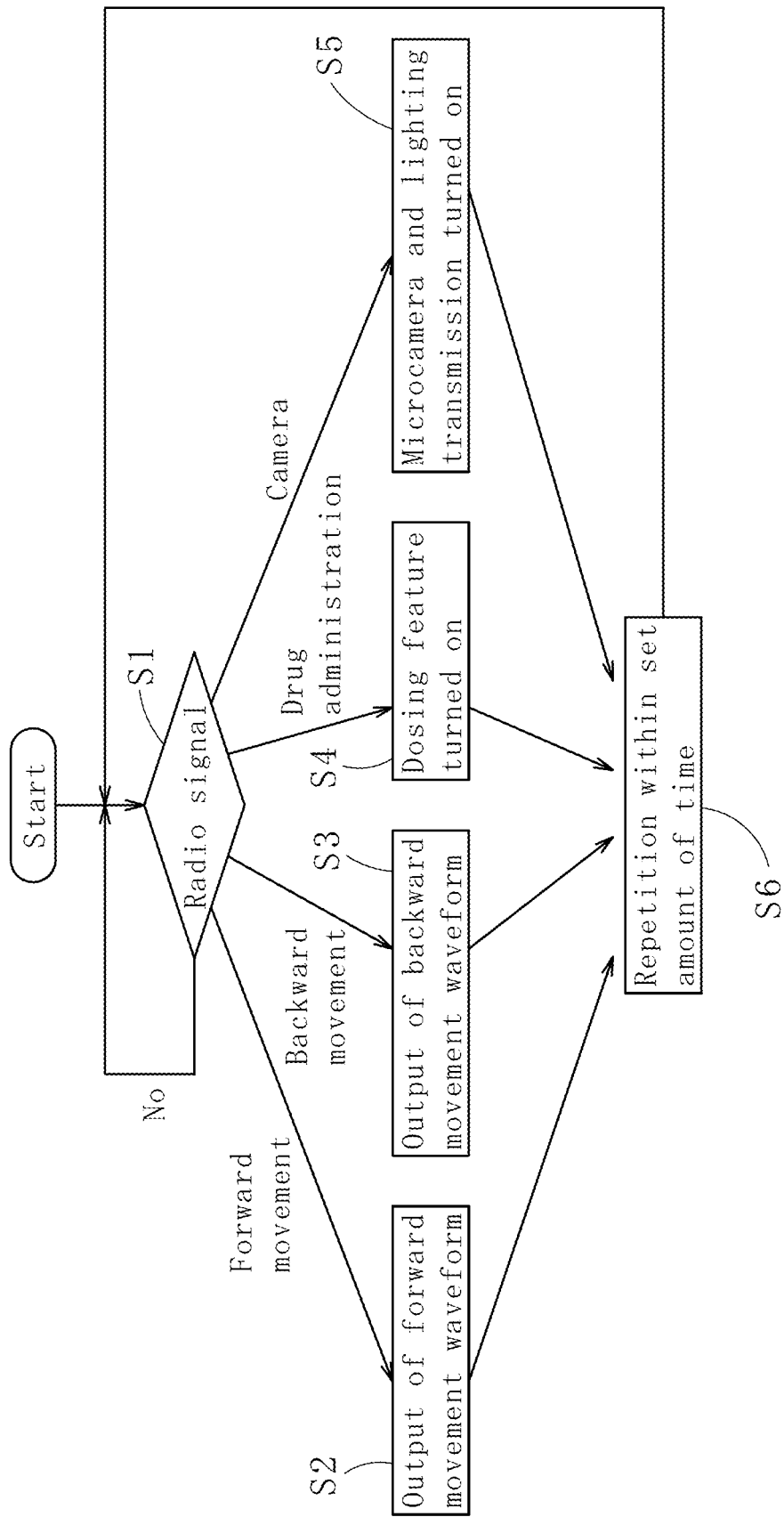
FIG. 9 is a motion flow chart of the mobile capsule device.

FIG. 9 illustrates an operational flow of a capsule device 35. A coil 42 that operates as an antenna receives radio waves from an external radio signal transmission device 64. The radio waves are transmitted to a radio signal receiving circuit 61a, and converted to digital signals and transmitted to a control part 48. The control part 48 identifies commands in the radio signals (Step S1). Among the commands are "forward movement," "backward movement," "drug administration," and "camera." In the case of "forward movement," an alternating current superposed by a direct current from a second output part 60 in a positive direction is applied to the coil 42, and a capsule device 35 moves forward. In the case of "backward movement," an alternating current superposed by a direct current in a negative direction is applied to the coil 42.

If a command of "drug administration" is received, a signal is sent to a first output part 59 in order to activate a dosing feature. Also, if a command of "camera" is received, an LED for lighting 57 is turned on and a microcamera 50 becomes activated. The received signals from the microcamera 50 are externally transmitted through an image transmission circuit 56 and antenna 62. There is an unillustrated image-receiving device on the outside, and images photographed by the microcamera 50 are successively recorded and output (Steps S2 to S5). The above operations are finished within a set amount of time, and the capsule device 35 goes back to the start and awaits radio signals (Step S6).

Moreover, a moving speed of the capsule device 35 can be estimated in the same manner as the capsule device 10. The constitution of the present invention may be changed freely without departing from the scope of the present invention. For example, in the capsule device 10 according to the first embodiment, the first and second coil parts are arranged symmetrically to the cylinder-shaped body, however, one coil part can be placed in a position slightly posterior/anterior to the other as well. Additionally, in some cases, the first and second coil parts can be connected in parallel with one another, and the number of turns in the first and second coil parts can also be changed. Furthermore, the explanations are given by using concrete figures in the foregoing embodiment, however, the figures may be changed as well without departing from the scope of the present invention.

Two permanent magnets are used in the capsule device 35 according to the second embodiment, however, the number of permanent magnets can be changed to one or even 3 or more, and the lengths of a plurality of permanent magnets can be the same or changed. The number of the coil 42 used for the capsule device 35 according to the second embodiment is one, however, the coil can be divided into two halves in a longitudinal direction apart from one another so as to be coil parts 1 and 2.

Additionally, in the first and second embodiments, inside of a capsule body is the same as air pressure, however, a pressure can be decreased, which consequently improves the movements of the permanent magnets and the coils.

The present invention is also applicable under the situations where a part of the capsule device 10 according to the first embodiment is applied to the capsule device 35 according to the second embodiment, and where a part of the capsule device 35 according to the second embodiment is used for the capsule device 10 according to the first embodiment.

INDUSTRIAL APPLICABILITY

By using a capsule device according to the present invention, a mobile capsule for the interior of gastrointestinal tracts that travels inside gastrointestinal tracts used for medical examinations and treatments can be completed. Moreover, compared to the case where a capsule drifts naturally inside gastrointestinal tracts, the capsule device is capable of moving independently, which enables the capsule to travel without damaging the interior of gastrointestinal tracts and reach targeted observation/treatment sites in a short amount of time. Additionally, this capsule device can also be utilized for collecting cells for the diagnosis of gastrointestinal tracts while wirelessly communicating with the outside.

REFERENCE SIGNS LIST

10: mobile capsule device, 11: capsule body, 12: cylinder-shaped body, 13: permanent magnet, 15, first coil part, 16: second coil part, 17, 18: stopper, 24: capsule device, 25: actuator, 26: battery, 28: microcamera, 29: position sensor, 30: control device, 31: radio, 32: capsule body, 35: mobile capsule device, 36: capsule body, 36a: cylindrical portion, 36b, 36c: lid portion, 27, 38: supporting member, 39, 40: permanent magnet, 41: bobbin, 42: coil, 44: cylindrical portion, 45, 46: flange, 47a, 47b: middle hole, 48: control part, 48a, 48b: platform, 50: microcamera, 51: instrument for procedures, 52: dosing feature, 53: battery, 54: storage portion, 55: MPU, 56: image transmission circuit, 57: LED for lighting, 59: first output part, 60: second output part, 61: position sensor, 61a: radio signal receiving circuit, 62: antenna, 64: radio signal transmission device

The invention claimed is:

1. A mobile capsule device, comprising:
a long capsule body provided with a permanent magnet and a coil, the permanent magnet being movable in the lengthwise direction with respect to the capsule body, the coil driving the permanent magnet, the coil being applied an alternate current through an alternate current generating means to perform a back and forth vibration of the permanent magnet and generate a propulsion force,
wherein the coil has first and second coil parts arranged in a forward and a backward motion of the permanent magnet so as to surround the permanent magnet, and a frequency of an alternate current applied to the first and second coil parts corresponds to a resonance frequency of the capsule device generated by a back and forth vibration of the permanent magnet,
the first and second coil parts are wound around a cylinder-shaped body having a slight interspace between the cylinder-shaped body and the permanent magnet to enable movement of the permanent magnet inside the cylinder-shaped body,
the cylinder-shaped body wound by the first and second coil parts is inside the capsule body and the capsule device,
stoppers are arranged on both sides of the cylinder-shaped body,
an alternate current generated by the alternate current generating means is composed of a positive/negative symmetrical alternate current further added by a direct current,
an excitation force generated by the first and second coil parts and the permanent magnet is intensified in one direction,
the moving direction of the capsule device is determined based on a polar character of the direct current,
by an electromagnetic force generated by the first and second coil parts, the permanent magnet performs a back and forth vibration while crashing into the stoppers, and
the resonance frequency is a frequency at which an electric current value becomes minimum when an alternate current is actually applied to the first and second coil parts.

2. The mobile capsule device as set forth in claim 1, wherein the capsule body is provided with a radio which liaises with an external control device.

3. The mobile capsule device as set forth in claim 2, wherein the coil is used as an antenna for the radio.

4. The mobile capsule device as set forth in claim 1, wherein the capsule body is provided with one or more of the following: an illuminated microcamera, instrument for procedures, dosing feature and position sensor.

5. A method for controlling a mobile capsule device having a long capsule body provided with a permanent magnet and a coil, the permanent magnet being movable in the lengthwise direction with respect to the capsule body, the coil driving the permanent magnet, the coil being applied an alternate current to perform a back and forth vibration of the permanent magnet and generate a propulsion force, the method comprising:
determining the moving direction of the capsule body by making a frequency of an alternate current applied to the coil accord with a resonance frequency of a back and forth vibration of the permanent magnet, and superposing a direct current on the alternate current,
wherein the coil is divided for first and second coil parts each arranged in a forward and a backward motion of the permanent magnet so as to surround the permanent magnet, the first and second coil parts further wound around a cylinder-shaped body having an interspace between the permanent magnet and the cylinder-shaped body to enable movement of the permanent magnet inside the cylinder-shaped body,
the cylinder-shaped body wound by the first and second coil parts is inside the capsule body and the capsule device, and
by an electromagnetic force generated by the first and second coil parts, the permanent magnet performs a back and forth vibration with respect to the cylinder-shaped body.

6. The method for controlling a mobile capsule device as set forth in claim 5, wherein
an inner portion of the capsule body is provided with one or more of the following: an illuminated microcamera, instrument for procedures, dosing feature, and position sensor; and
controls are performed by a radio using the coil as an antenna and a control part connected to the radio.

* * * * *